United States Patent [19]

Richards et al.

[11] Patent Number: 5,771,894
[45] Date of Patent: Jun. 30, 1998

US005771894A

[54] NON INVASIVE IDENTIFICATION OF INTESTINAL ISCHEMIA FROM MEASUREMENT OF BASIC ELECTRICAL RHYTHM OF INTESTINAL SMOOTH MUSCLE ELECTRICAL ACTIVITY USING A MAGNETOMETER

[75] Inventors: William O. Richards, Nashville; John P. Wikswo, Jr., Brentwood; Daniel J. Staton, Nashville, all of Tenn.; Javad Golzarian, Stoneybrook, N.Y.; Leonard A. Bradshaw, Nashville, Tenn.

[73] Assignee: Vanderbilt University, Nashville, Tenn.

[21] Appl. No.: 847,838

[22] Filed: Apr. 28, 1997

Related U.S. Application Data

[63] Continuation of Ser. No. 461,721, Jun. 5, 1995, abandoned.
[51] Int. Cl.⁶ ........................................................ A61B 5/05
[52] U.S. Cl. ...................................... 128/653.1; 128/691
[58] Field of Search ................................ 128/653.1, 691; 324/244, 248

[56] References Cited

U.S. PATENT DOCUMENTS 3,980,076  9/1976  Wikswo, Jr. et al. ................... 128/128
4,079,730  3/1978  Wikswo, Jr. et al. ................... 128/128

OTHER PUBLICATIONS

*Myoelectric Assessment of Bowel Viability*; R.Brolin, J.Semmlow, R.Koch, M.Reddell, B.Mast, J.Mackenzie; From the Department of Surgery, University of Medicine and Dentistry of New Jersey; vol. 102; Jul. 1987; pp. 32–38.

*The Effects of Ischemia on the Electrical and Contractile Activities of the Canine Small Intestine*; R.Cabot, S.Kohatsu, From the Department of Surgery, VA Hospital, Palo Alto, and Stanford University School of Medicine; Aug. 1978; pp. 242–246.

The Effects of Ischemia on Intestinal Nerves and Electrical Slow Waves; J.Khin Kyi Kyi, and E.E. Daniel; Digestive Diseases, vol. 15, No. 11; Nov. 1970; pp. 959–981.

*Electromyography to Determine Viability of Injured Small Bowel Segments: An Experimental Study with Preliminary Clinical Observations*; M.Schamaun, Zurich, Switzerland; From the Dept. of Surgery A.Kantonsspital and the Univ. of Zurich Medical School; vol. 62, No. 5, pp. 899–909.

*The Use of Intraperitoneal Xenon for Early Diagnosis of Acute Mesenteric Ischemia*; F.Ghaaragozloo,G.Bulkley, G.Zuidema, C.O;Mara, P.Alderson; From the Dept. of Surgery and Radiology, The Johns Hopkins Medical Institutions, Apr. 1984; pp. 404–411.

*Non–Invasive Squid Magnetometer Measurement of Human Gastric and Small Intestinal Bowel Electrical Activity*; W.richards, D.Staton, J.Golzarian, R.Friedman, J. Wikswo, Jr.;International Meeting on biomagnetism in Vienna, Austria; Aug. 1993; pp. 1–6.

(List continued on next page.)

Primary Examiner—Ruth S. Smith
Attorney, Agent, or Firm—Richard V. Westerhoff; Eckert Seamans Cherin & Mellott, LLC

[57] ABSTRACT

Intestinal ischemia is diagnosed non-invasively by scanning the abdomen externally with a SQUID magnetometer which measures the magnetic field produced by smooth muscle electrical activity. These measurements are processed to determine the basic electrical rhythm (BER) frequency at various locations along the intestine. A nominal value for the BER frequency is established at each location, and if the measured value falls below the associated nominal value by more than a predetermined margin, ischemia at that location is indicated. Ischemia is further indicated by an interval of arrhythmia in which the BER frequency increases to a range of about 24–180 cpm or at least about twice the nominal value. The BER frequency values are presented on a graphic display which provides an indication of the nominal value at an affected location from the gradient of the measured values at adjacent normal locations. Also, a gradual reduction in the local BER frequency at a particular location is an indication of progressive ischemia, while an absence of BER activity in a section of intestine indicates necrosis.

24 Claims, 5 Drawing Sheets

OTHER PUBLICATIONS

*Gastrointestinal System; Physiology, Pathology, and Possibilities for Biomagnetic Diagnosis*; W.Richards, J. Wikswo, Jr., International Meeting on biomagnetism in Vienna, Austria; Aug. 1993; pp. 1–6.

*Measurements of Small Bowel Electrical Activity in Vivo Using a High–Resolution Squid Magnetometer*; D.Staton, J.Golzarian, J.Wikswo, Jr., R.Firedman, W.Richards; International Meeting on Biomagnetism in Vienna, Austria; Aug. 1993; pp. 1–4.

*Interpreting Magnetic Fields of the Brain: Minimum Norm Estimates*; M.S. Hamalainen and R.J. Ilmoniemi; Med. & Biol. Eng. & Comp., 32, 35–42, 1994.

*Multiple Dipole Modeling and Localization from Spatio–Temporal MEG Data*: J.Mosher, P.Lewis and R.Leahy; IEEE Trans. Biomed. Eng., 39,541–557, 1992.

*Continuous Probabilistic Solutions to the Biomagnetic Inverse Problem*: A.Ioannidest, J.Bolton and C.Clarke; Inverse Proglems, 523–542, 1990.

*Using a Magnetometer to Image a Two–dimensional Current Distribution*: B.Roth, N.Sepulveda and J.Wikswo, Jr.; J.Appl.Phys. 65, 361–372, 1989.

*3–Dimensional Biomagnetic Localization of Electric Activity of the Human Stomach—A New Non–Invasive Diagnostic Approach?*; H.D.Allescher, K.Abraham–Fuchs, P.Wegener, S.Schneider, Dept. of Internal Medicine II, Technical Univ.Munich, Germany; *Motility and Nerve–Gut Interactions*; Apr. 1992; p. A415.

A Biomagnetic Method for Studying Gastro–Intestinal Activity; S.DiLuzio, S.Comani and G.L.Romani, M.Gasile, C.Del Gratta and V.Pizzella; *Il Nuovo Cimento*: vol. 11D, N.12; Dec. 1989; pp. 1853–1859.

*Extracorporeal Direct Magnetic Measurement of Gastric Activity*; S.Comani, M.Basile, S.Casciardi,C.DelGratta, S.DiLuzio, S.N. Erne, M.Macri, M.Neri, M.Pereresson, and G.L. Romani; 1992 Biomagnetism; Clinical Aspects; pp. 639–642.

*The Biomagnetic Approach to the Study of Gastrointestinal Activity*; G.D'Annunzio; 1992 Biomagnetism; Clinical Aspects; pp. 613–629.

*Intraoperative Determination of Small Intestinal viability Following Ischemic Injury*; G.Bulkley, G.Zuidema, S.Hamilton,C.OMara, P.Klacsmann, S.Horn; Presented at Annual Meeting of the Southern Surgical Association; Dec. 1980; pp. 628–635.

*The Use of Surface Oximetry to Assess Bowel Viability*; R.Locke, C.Hauser, W.Schoemaker; Arch Surg–vol. 119; Nov. 1984; pp. 1252–1256.

*The Use of Infrared Photoplethysmography in Identifying Early Intestinal Ischemia*; W.Pearce, D.Jones, G.Warren, E.Bartle, T.Whitehill, R.Rutherford; Arch Surg–vol. 122, Mar. 1987; pp. 308–310.

Squid Magnetometer Diagnosis of Experimental Small Bowel Ischemia, D.J. Straton et al., Vanderbilt University and Department of Surgery, Veterans Administration Medical Center, 0–7803–1377–Jan. 1993 (1993).

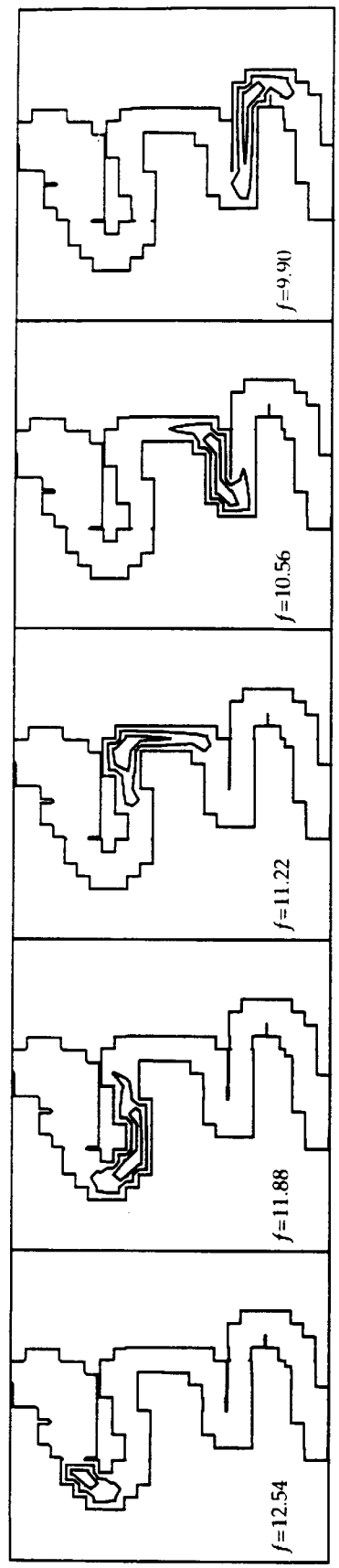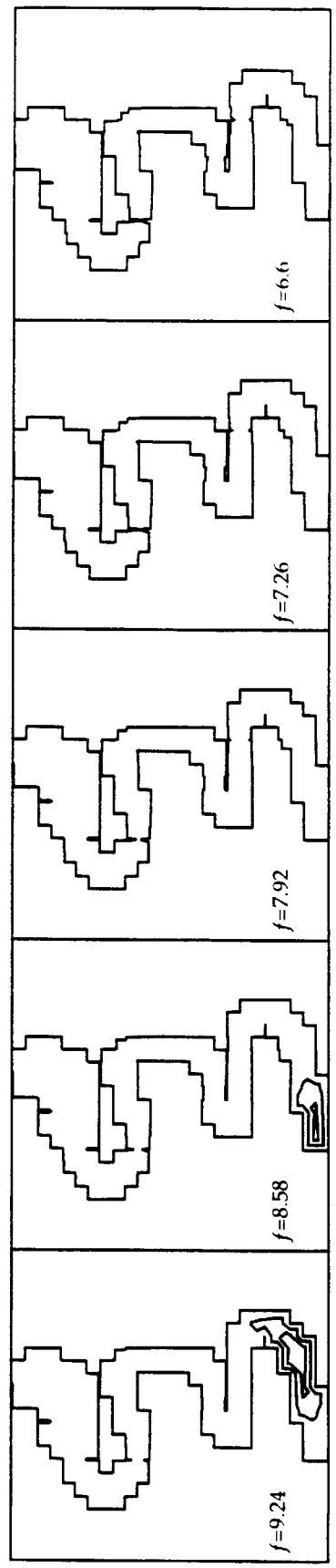

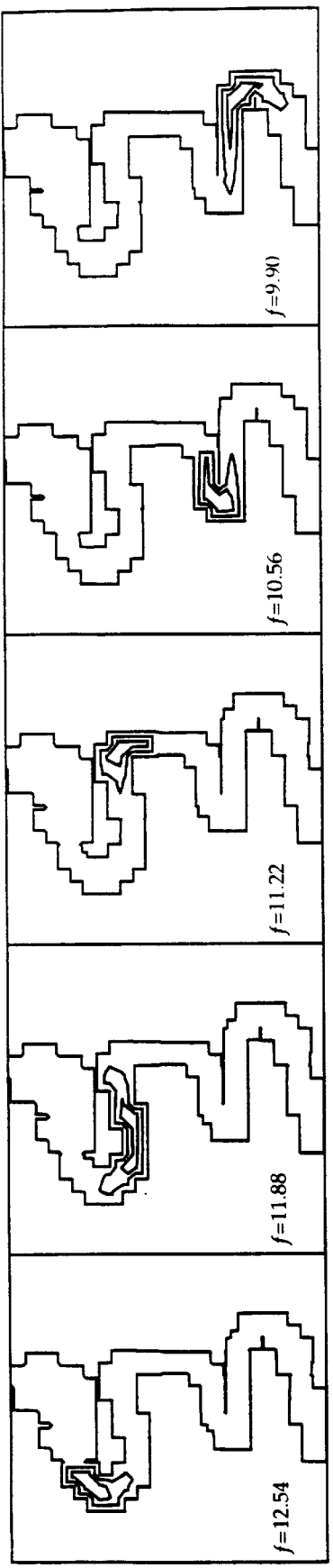
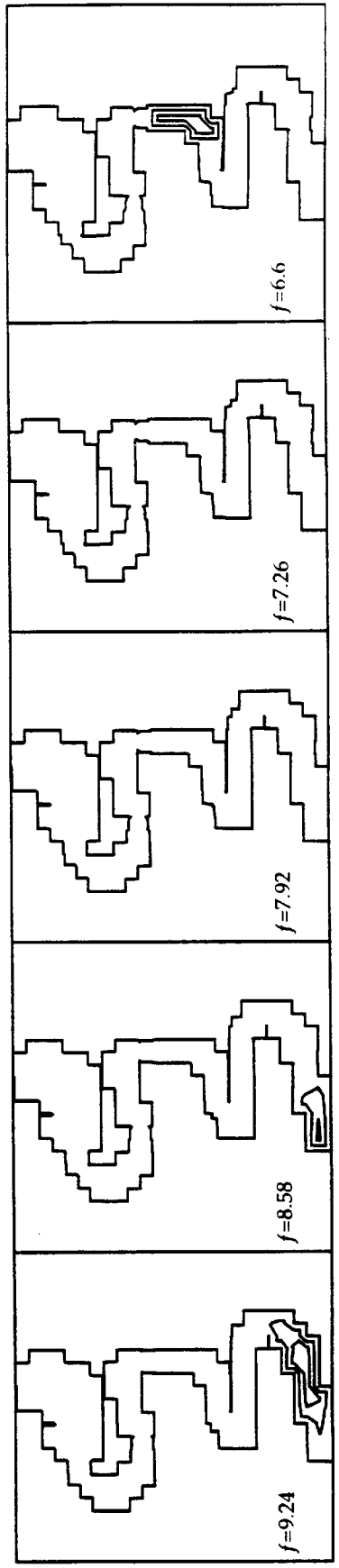

NON INVASIVE IDENTIFICATION OF INTESTINAL ISCHEMIA FROM MEASUREMENT OF BASIC ELECTRICAL RHYTHM OF INTESTINAL SMOOTH MUSCLE ELECTRICAL ACTIVITY USING A MAGNETOMETER

This application is a continuation, of application Ser. No. 08/461,721, filed June 5, 1995, now abandoned.

This invention was made with government support under grant NS24751, awarded by the National Institutes of Health, and a grant awarded by the Department of Veterans Affairs Research Service. The government has certain rights in the invention.

BACKGROUND OF THE INVENTION

1. Field of the Invention

This invention relates to a method and apparatus for a non-invasive diagnosis of ischemia of the small and large intestine using magnetometers, and particularly a Super conducting QUantum Interference Device (SQUID) magnetometer.

2. Background of Information

Ischemia (lack of blood flow) of the smooth muscles of the small and large intestine (collectively referred here throughout for convenience as "intestine") is an acute surgical emergency associated with mortality rates of 70 to 90%.

Over the past two decades it has become clear that the best patient outcomes can be achieved if prompt intervention can be started before widespread necrosis has occurred. However, the principal problem with this approach is the lack of a non-invasive, sensitive diagnostic test that can detect acute ischemia before the development of smooth muscle necrosis. The most useful diagnostic test has been mesenteric angiography which is both invasive and time consuming. Another disadvantage of angiography is that it measures blood flow and not the viability of the intestine. Less invasive options such as tests for leukocytosis and metabolic acidosis are available, but these conditions are present in almost all major abdominal surgical emergencies. Elevations in alkaline phosphatase, lactic dehydrogenase, creatinine phosphokinase, and liver transaminase have been described, however, these changes occur late in the course of disease which, unfortunately, indicates that necrosis of intestinal cells has already taken place, thus limiting their usefulness for early detection. Intraperitoneal radioisotope xenon scanning was useful in animal experiments but has not proved useful in clinical practice. Several other diagnostic studies including duplex ultrasound scanning, and magnetic resonance imaging (MRI), are somewhat promising although none has yet been established for clinical use. The major problem with the ultrasound study is that it measures blood flow and not the viability of the bowel itself. Moreover, this test relies on visualizing the major vessels and thus is limited to evaluation of large vessel disease. Finally, this test can be obscured by the overlying bowel gas that occurs frequently with ischemia. MRI scanning relies on visualizing the accumulation of intracellular and extracellular fluid caused by arterial occlusion. Since many other disease processes also induce bowel edema, a false positive study may be commonly seen in clinical practice. Finally, these MRI changes only occur after pathologic changes, thus they would not detect the early phase of ischemia while the ischemic changes are still reversible.

Several investigators have reported the effects of ischemia on small bowel electrical activity. These effects include a reduction in frequency and amplitude of the Basic Electrical Rhythm (BER), although it returns following reperfusion. If the ischemia continues long enough for the smooth muscle fibers to die, the BER is lost altogether. The decreases in BER frequency occur within minutes after acute arterial occlusion and thus can be identified long before pathologic changes can be identified. These changes in the electromagnetic wave forms were noticed within 5 to 10 minutes of ischemia; in contrast, the earliest evidence of histopathologic changes in the muscle could not be detected until 60 minutes after onset of ischemia. These studies on the effects of ischemia required surgical implantation of electrodes and thus were invasive.

There is a need for an improved method and apparatus for reliably, non-invasively diagnosing ischemic intestine.

Preferably, there is a need for such non-invasive diagnosing of ischemic intestine which does not require the use of ionizing radiation so that it can be used with pediatric patients and pregnant women also.

There is a need for such an improved diagnosis of ischemic intestine which provides sufficient warning for intervention before irreversible pathology occurs.

SUMMARY OF THE INVENTION

These needs and others are satisfied by the invention which is directed to non-invasive diagnosis of intestinal ischemia by measuring the magnetic field produced by smooth muscle electric activity in an intestine in vivo within an abdomen. More particularly, the invention comprises measuring a measured value of the local basic electrical rhythm (BER) frequency from the magnetic field produced by the smooth muscle electrical activity at at least one location external to the abdomen. A nominal value for the local BER frequency is established at the at least one location and intestinal ischemia is identified at the at least one location when the measured value of the local BER frequency differs from the nominal value by a predetermined margin. Ischemia is indicated when the local BER frequency falls at least about 20%, below the nominal value. We have also discovered that in many instances the reduction in the BER frequency is accompanied by an interval of arrhythmia in which the BER frequency temporarily increases to a level at least two (2) times the nominal BER frequency, in a range of about 24 to 180 cpm.

Preferably, the local BER frequency is measured for a plurality of areas across the abdomen and a nominal BER frequency is established for each area so that an area in which ischemia is present can be identified if the measured value of the BER frequency for the area falls below an associated nominal value by more than the selected margin. As the nominal value of the BER frequency decreases from the proximal to the distal end of the intestine, the nominal value of the BER frequency in an array of locations along the intestine can be established as a decreasing trend. This decreasing trend can be established from the measured values of BER frequency along the intestine. A decrease in a local BER frequency of more than about 20% below the trend, and/or detection of an arrhythmia at a location along the intestine, is an indication of ischemia.

There are different grades of ischemia, and thus, a progressive decline in BER frequency is just as important as an absolute number. As the technique is noninvasive, long term monitoring is practical and suitable for detection of progressive onset of ischemia. Furthermore, an absence of BER activity in a section of intestine is diagnostic of dead bowel indicating the ischemia has progressed to necrosis requiring an emergency operation.

Preferably, the apparatus for carrying out the invention includes a display for visually presenting the BER frequency information. The SQUID magnetometer is particularly useful for detecting the very weak magnetic fields generated by the smooth muscle electrical activity in the intestine. A hand-held SQUID magnetometer can be used to scan the abdomen and thus generate BER frequency measurements for a portion of or across the entire abdomen. Preferably, a large array of SQUIDS can be used to measure the BER frequencies across the entire abdomen.

The signals generated by the SQUIDS are processed to generate the dominant BER frequency at an array of locations. The display can present on a single screen the distribution of these dominant BER frequencies. The decrease in the trend in the BER frequency from the proximal to the distal end will be evident from this display, and any deviation from the trend will indicate the location of an ischemic segment. In an alternate display, a series of screens each displaying the location of a different dominant frequency is presented. An observation of these screens will indicate the area of ischemia by a dominant frequency which is out of order with regard to the trend.

BRIEF DESCRIPTION OF THE DRAWINGS

A full understanding of the invention can be gained from the following description of the preferred embodiments when read in conjunction with the accompanying drawings in which:

FIGS. 5a–j illustrate a series of screens generated in accordance with another embodiment of the invention and showing the normal intestine without ischemia.

FIGS. 6a–j are similar to those of FIGS. 4a–j illustrating ischemia in the same location as in FIG. 4.

DESCRIPTION OF THE PREFERRED EMBODIMENT

The invention is directed to a method and apparatus for non-invasively diagnosing ischemia in the intestine of humans and animals. It is known that the basic electrical rhythm (BER) frequency of the intestine slowly decreases from the proximal to the distal end. In humans, the BER frequency at the proximal end is about 12.0 cpm and about 8 cpm at the distal end. For rabbits, on which many experiments have been performed, the BER frequency ranges from about 16 at the proximal end to about 12 at the distal end.

Ischemia, or lack of blood flow to the intestine or a section of the intestine can be caused by an embolus or thrombosis, or may be the result of a strangulating mechanical bowel obstruction. In any case, acute intestinal ischemia is a highly lethal condition.

Figure 1:
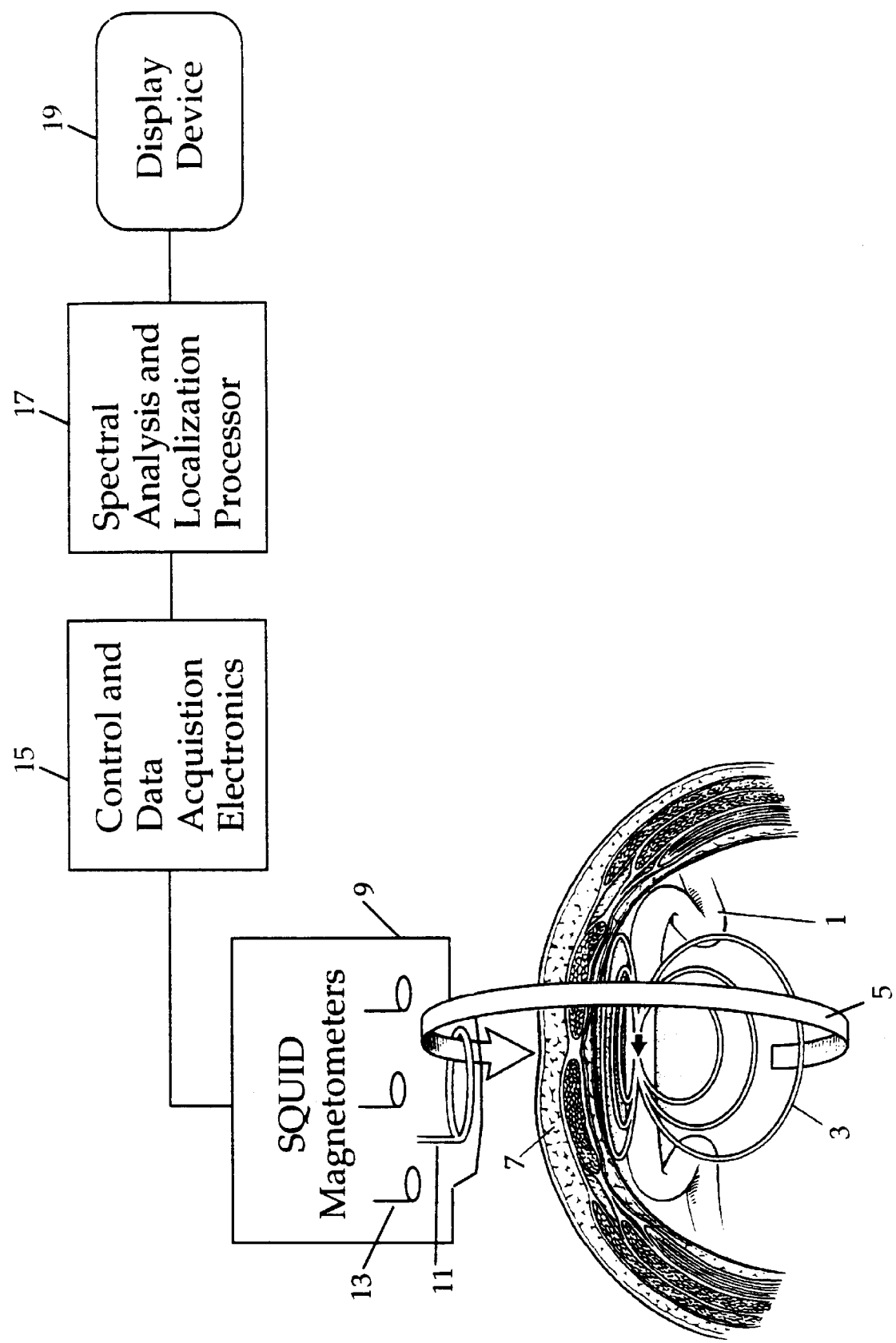
FIG. 1 is a schematic diagram illustrating apparatus in accordance with the invention for non-invasively diagnosing intestinal ischemia in a patient shown schematically partially in section.

As shown in FIG. 1, small muscle electrical activity within the intestine 1 generates an electric field 3 which induces a magnetic field 5. With the intestine 1, in vivo, within the abdomen 7 the magnetic field is detected externally of the abdomen, and without surgical intervention or penetration of any kind. This magnetic field is measured by a magnetometer 9. The magnetometer is preferably a Super conducting Quantum Interference Device (SQUID) magnetometer. A particular SQUID magnetometer available is the SQUID high-resolution SQUID magnetometer developed by the Living State Physics Group at Vanderbilt University. The MicroSQUID contains an array of four SQUIDS with pickup coils such as 11 (only one shown) arranged at the corners of a 4.4 mm square. The MicroSQUID permits the pickup coils 11 to be brought within 2 mm of the tissue. Such a magnetometer can detect fields as small as one-billionth the strength of the earth's magnetic field. A single hand-held MicroSQUID can be used to scan over the surface of the abdomen 7 to detect the magnetic field at a plurality of locations. However, preferably an array 13 of pickup coils and associated SQUIDS can be used to make measurements at an array of locations simultaneously. Such an array 13 can be scanned across the abdomen, or if the array is large enough, can be scanned electronically to generate measurements of the magnetic field at an array of locations across the abdomen.

Figure 2:
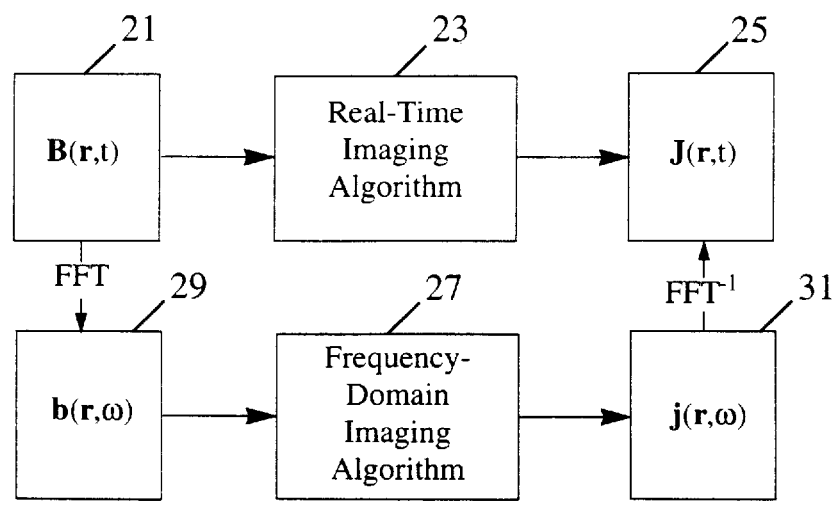
FIG. 2 is a diagram illustrating alternative approaches to generating displays using the apparatus described in FIG. 1.

The control and data acquisition electronics 15 control the operation of the magnetometer and preprocessing of the measurements generated by SQUIDS for analysis. This preprocessing includes digitizing the signals for processing by digital processor 17, and can include filtering to remove noise such as the generally 3 cpm BER generated by the stomach, and electrical activity of the heart (nominally 72 cpm). As an alternative to filtering the heart electrical activity, an electrocardiogram (EKG) can be taken and subtracted from the magnetometer signal. The digital signals are then processed by the processor 17 which performs spectral analysis on the magnetic measurements and associates them with the local areas of the abdomen. The results are displayed on a display device 19. A display provides a convenient way of presenting the results. The choice of an imaging algorithm to reconstruct the source of current distribution from the magnetic field measurements is an important step in evaluating the electrical activity of the intestine. As illustrated in FIG. 2, there are several ways to perform the reconstruction from the magnetic measurements 21 recorded by the SQUID. The most straightforward way is to use an imaging algorithm 23 on the measured data in real time to reconstruct a time sequenced current distribution 25. However, information about ischemia is more readily ascertained from inspection of the frequency-domain data. Thus, a similar frequency domain imaging algorithm 27 can be applied to frequency-decomposed magnetic field data 29 generated from the magnetic field data 19. The result is a frequency-sequenced current distribution 31. This frequency-sequenced distribution 31 could then be transformed, if desired, to reproduce a time-sequenced current distribution 25.

The time-domain imaging algorithm 23 would typically be an inverse solution to the law of Biot-Savart. This can be done in several ways, including comparison of the measured magnetic field pattern with magnetic field patterns from known source current distributions, and adjusting the source distribution to obtain the best fit in a least-squares sense. Workers in the field of magnetoencephalography have developed numerous inverse algorithms that would be applicable in magnetoenterography as well. For example, see: Hamalainen, J., and R. Ilmoniemi, "Interpreting magnetic fields of the brain: Minimum norm estimates," Med. & Biol.

Eng. & Comp., 32, 35–42, 1994, and Mosher, J., P. Lewis and R. Leahy, "Multiple dipole modeling and localization from spatial-temporal MEG data", *IEEE Trans. Biomed. Eng.*, 39, 541–557, 1992. Alternative solutions include: Ioannides, A., J. Bolton, and C. Clarke, "Continuous probabilistic solutions to the biomagnetic inverse problem", *Inverse Problems*, 523–542, 1990 and Roth, B., N. Sepulveda, and J. P. Wikswo, Jr., "Using a magnetometer to image a two-dimensional current distribution," *J.Appl. Phys.*, 65, 361–372, 1989. Although these algorithms are all designed to produce single time-sliced current reconstructions from single time-sliced magnetic field data, they could be adapted to work with frequency-domain magnetic data as shown in FIG. 2. It should be emphasized that the purpose of applying an imaging or inverse algorithm in the frequency domain is to generate maps of the frequency-domain current distribution in specific frequency bins, thus effectively band pass filtering the magnetic field data, and hence, the source reconstructions. This allows visualization of the areas of the intestine that are "active" over a narrow frequency range.

Figure 4:
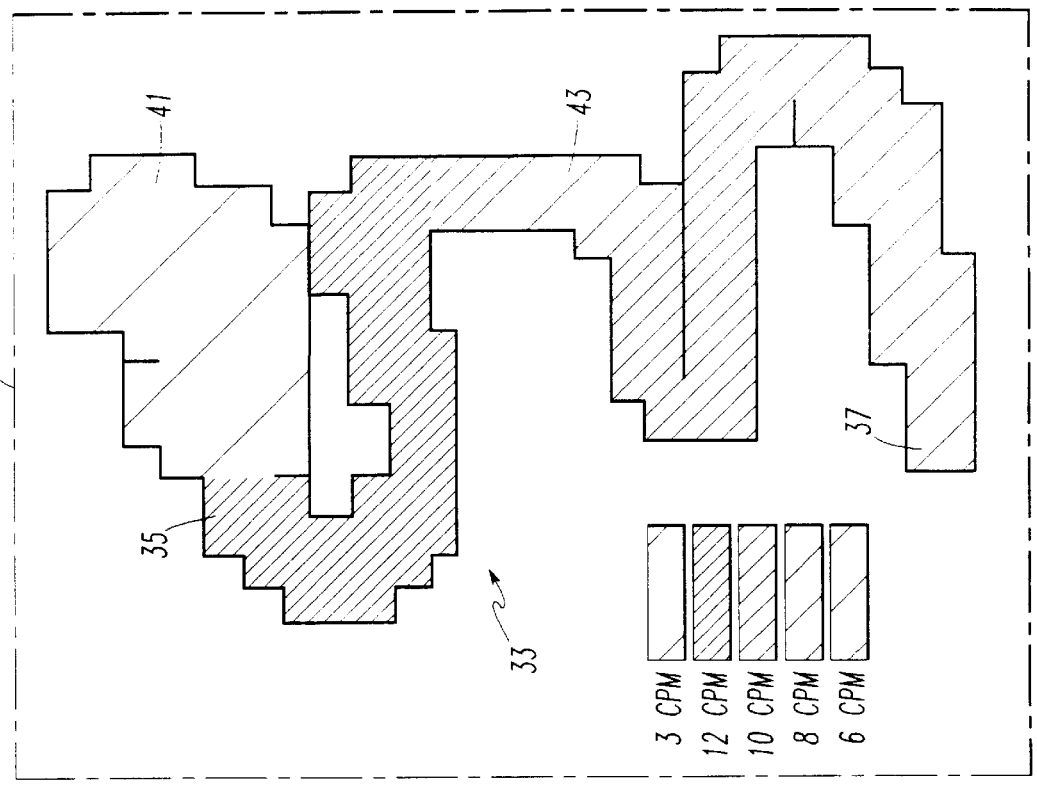
FIG. 4 is a diagram illustrating a screen which can be generated with the invention illustrating an intestine with an ischemic section.
Figure 3:
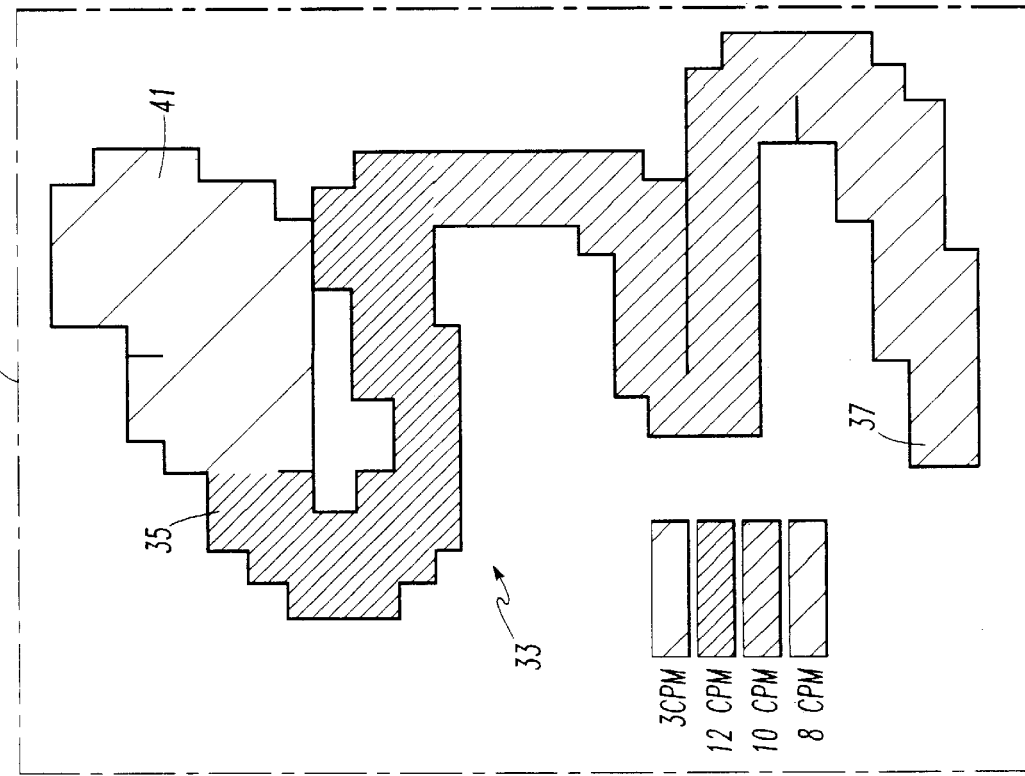
FIG. 3 is a diagram illustrating a screen which can be generated using the invention to display a normal intestine without ischemia.

Screens using hypothetical data to produce examples of frequencydomain images of the intestine 33 which can be generated on the display device 19 in accordance with the invention are shown in FIGS. 4, 5a–j, and 6a–j. A BER frequency of 12 cpm was used for the proximal end 35 of the intestine and 8 cpm was used for the distal end 37. FIGS. 3 and 4 illustrate presentation on the screen 39 of the dominant frequency recorded in one map for two different conditions. The stomach 41 depicted at the top of FIGS. 3 and 4 is shown to have a BER frequency of 3 cpm. FIGS. 5a–j and 6a–j illustrate separate screens a–j for the spectral decomposition of the magnetic field at several frequency bins, again for two different conditions. In FIGS. 3 and 5a–j which represent a normal intestine, there is a steady gradient from a 12 cpm BER at the proximal end to the 8 cpm BER at the distal end. While variable shading has been used in FIGS. 3 and 4 to indicate the measured BER frequency along the intestine, color could alternatively be used to indicate local BER frequency.

FIGS. 4 and 6a–j illustrate an intestine with an ischemic section about mid-way between the proximal and distal ends. As can be seen in FIG. 4, where the dominant frequency is generally indicated by the legend accompanying the graphic representation of the intestine, the dominant frequency goes from 10 to 6 and then back to 10 at about the midpoint between the proximal and distal ends. The dominant frequency of 6 indicated at 43 marks the location of the ischemia. FIG. 6a–j illustrates an ischemia at the same location. From FIGS. 6a, b and c, it can be seen that the successive dominant frequencies represented by the screens occupy continuous sections of the graphic illustration of the intestine. However, it can be seen from FIGS. 6c and 6d which illustrate a dominant frequency of 11.22 cpm and 10.56 cpm, respectively, that there is a gap in the illustration of the dominant frequency. It can be seen from FIG. 6j that the dominant frequency in this gap is 6.6, which again, indicates an ischemic section.

It can be appreciated from the above that the graphic presentation of the frequency domain data provides a convenient arrangement for detecting ischemic sections of the intestine. The presentation of the dominant frequency along the entire, or an extended section of the intestine provides a reference for the nominal values of the BER frequency in any particular section. The decrease in the trend in the BER frequency from the proximal to the distal end provides the reference for what the expected value of the BER frequency would be at intermediate points. If the artery supplying blood to the intestine is occluded so that the entire intestine becomes ischemic, the known nominal value of approximately 12 at the proximal end and 8 at the distal end with a steady gradient between provides the reference for diagnosing the condition. A BER frequency which is about 20% or more below the nominal value is a reliable indicator of an ischemic section of the intestine. This reduction in the BER frequency normally occurs within about 5 to 10 minutes of the occlusion. As necrosis does not occur until at least an hour after occlusion, the present technique provides a convenient non-invasive tool for diagnosing an ischemia so that appropriate treatment can be administered before the condition becomes irreversible. As mentioned previously, since the technique of the invention is non-invasive and also uses no ionizing radiation, it can be used over an extended period of time such as for post operative monitoring where an increase in the BER frequency would indicate a successful reperfusion. It can also be used to detect a progressive reduction in BER frequency for a given section of the intestine which would be indicative of mesenteric ischemia. Also as mentioned, an absence of BER activity (a black hole) in the midst of active intestine would be indicative of a dead section of intestine requiring an emergency operation.

We have also found that the reduction in the BER frequency can be accompanied by an interval of arrhythmia in which the BER increases to at least about twice the nominal value of BER frequency for a given segment, and more likely for humans to a value of about 24 to 180 cpm. Arrhythmias occur in the intestine during acute ischemia, and if detected it is pathognomonic (absolutely diagnostic of an ischemic segment). Characteristically it occurs 15–20 minutes after induction of ischemia and occurs only in small segments of the intestine. Typically, we see an area of small bowel that has been ischemic for 15–20 minutes that transiently develops into this abnormal tachyarrhythmia that is most characteristically approximately 120 cycles per minute (cpm) in rabbit experiments. This lasts for 2–5 minutes and does not persist for the duration of the ischemic period. Detection of such an arrhythmia would be diagnostic of an ischemic segment and further mapping of the intestinal magnetic fields would be unnecessary for diagnosis of ischemia. These tachyarrhythmias are detected in the same fashion that the change in BER frequency is detected in the remainder of the abdomen. Fast Fourier Transformation (FFT) or other spectral techniques can be performed on the data to identify the dominant frequency.

A number of techniques can be used to identify the tachyarrhythmias as being different from the cardiac activity. A variety of filtering techniques can be used to eliminate the contribution to the signal from the magnetic fields associated with cardiac electrical activity. Because these cardiac signals can be recorded independently as either the electrocardiogram (ECG) or the magnetocardiogram (MCG), it is possible to use synchronous filtering or subtraction techniques to eliminate the component of the magnetic signal recorded above the abdomen that is time-correlated with the ECG or MCG. Once the component that is correlated with the ECG or MCG is identified, it can then be subtracted. This process can be implemented as a classic adaptive filter, with adjustable filter weights, or with synchronized comb filter, for example.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

What is claimed is:

1. A non-invasive method of diagnosing intestinal ischemia from a magnetic field produced by smooth muscle electrical activity in an intestine in vivo within an abdomen, said method comprising the steps of:
    measuring the magnetic field produced by said smooth muscle electrical activity in said intestine at at least one location external to said abdomen;
    determining a measured value of local Basic Electrical Rhythm (BER) frequency from said magnetic field at said at least one location external to said abdomen;
    establishing a nominal value for said local BER frequency at said at least one location; and
    identifying intestinal ischemia at said at least one location when said measured value of local BER frequency at said at least one location differs from said nominal value for said local BER frequency by a predetermined margin and is accompanied by an interval of arrhythmia.

2. The method of claim 1 wherein intestinal ischemia is identified when said measured value of local BER frequency at said at least one location is at least about 20% below said nominal value and is accompanied by said interval of arrhythmia.

3. The method of claim 1 wherein said arrhythmia has a frequency of at least about 24 to about 180 cpm.

4. The method of claim 1 wherein said arrhythmia has a frequency of at least about twice said nominal BER frequency.

5. The method of claim 1 wherein said step of measuring comprises measuring a measured value of local BER frequency for each of a plurality of sections of said abdomen, said step of establishing comprises establishing an associated nominal value for said local BER frequency for each of said plurality of sections of said abdomen, and said step of identifying comprises identifying intestinal ischemia if said measured value of local BER frequency for any of said sections of said abdomen differs from the associated nominal value for said local BER frequency by a predetermined associated margin and is accompanied by said interval of arrhythmia.

6. The method of claim 5 wherein said step of identifying includes generating a display of said measured values of BER frequency for each of said sections of said abdomen.

7. The method of claim 5 wherein said predetermined associated margin is a decrease in the local BER frequency of at least about 20% below said associated nominal value for said local BER frequency.

8. The method of claim 5 wherein ischemia is identified when said measured value of local BER frequency falls below the associated nominal value for BER frequency in one of said sections of said abdomen and is accompanied by said interval of arrhythmia.

9. The method of claim 8 wherein said arrhythmia is an interval wherein said BER frequency increases to at least about twice the associated nominal value of said BER frequency for said section of said abdomen.

10. The method of claim 1 wherein said step of measuring comprises measuring local BER frequency at a plurality of locations generally in succession along at least one portion of said intestine in a direction toward an end of said intestine, wherein establishing nominal values of said BER frequency comprises establishing from said measured values at said plurality of locations generally in succession a general trend in said local BER frequencies in said direction toward said end, and wherein identifying ischemia comprises identifying intestinal ischemia at locations at which said measured value of local BER frequency differs from said general trend in local BER frequency by said predetermined margin and is accompanied by said interval of arrhythmia.

11. The method of claim 10 wherein said step of identifying comprises generating a display presenting said measured values of local BER frequency for said plurality of locations generally in succession.

12. The method of claim 10 wherein said step of identifying comprises identifying a location along said at least portion of said intestine as ischemic when the measured value of BER frequency at that location exhibits said arrhythmia.

13. The method of claim 1 wherein said step of measuring local BER frequency comprises measuring local BER frequency for a plurality of sections along said intestine, wherein said step of establishing nominal values comprises establishing a nominal value associated with each of said sections along said intestine from the local measured value of BER frequency for others of said locations, and wherein said step of identifying ischemia comprises identifying sections along said intestine as ischemic when the measured value of local BER frequency for a section differs from the associated nominal value for BER frequency for that section by said predetermined margin and is accompanied by said interval of ischemia.

14. Apparatus for analyzing a magnetic field produced by smooth muscle electrical activity in an intestine in vivo within an abdomen for use in non-invasive diagnosis of intestinal ischemia, said apparatus comprising:
    magnetometer means producing detected values of said magnetic field at at least one location across said abdomen;
    processing means generating from said detected values of said magnetic field measured values of local basic electrical rhythm (BER) frequency of said smooth muscle electrical activity at said at least one location including values associated with arrhythmia; and
    means presenting a representation of said measured values of local BER frequency including said values associated with arrhythmia.

15. The apparatus of claim 14 wherein said magnetometer means comprises a SQUID magnetometer.

16. The apparatus of claim 14 wherein said magnetometer means comprises an array of SQUID magnetometers producing a detected value of said magnetic field at an array of locations across said abdomen, wherein said processing means generates from said array of detected values of said magnetic field, an array of values for a local BER frequency at said plurality of locations, and wherein said means presenting a representation of said measured values of local BER frequency, presents a representation of said measured values of BER frequency at each of said plurality of locations.

17. The apparatus of claim 14 wherein said means presenting a representation of said measured values of BER frequency is responsive to values of BER frequency associated with arrhythmia from about 24 to about 180 cpm.

18. The apparatus of claim 14 wherein said means presenting a representation of said measured values of local BER frequency also provides an indication of a nominal value of said BER frequency.

19. The apparatus of claim 18 wherein said magnetometer means produces a detected value of said magnetic field at an array of locations across said abdomen, wherein said processing means generates a measured value of local BER frequency for each of said array of locations, and wherein said means presenting a representation of said measured values of local BER frequency presents a measured value of said local BER frequency for each of said locations.

20. The apparatus of claim 19 wherein said processing means comprises means generating a measure of dominant values of said local BER frequency at said array of locations, and wherein said means presenting a representation of said measured values of BER frequency generates a display indicating where in said array of locations said dominant values of BER frequency are located.

21. The apparatus of claim 20 wherein said means presenting a representation of said measured values of local BER frequency generates a display with a series of screens with each screen displaying the location in said array of a different one of said dominant BER frequency values.

22. A non-invasive method of diagnosing intestinal ischemia from a magnetic field produced by smooth muscle electrical activity in an intestine in vivo within an abdomen, said method comprising the steps of:

measuring the magnetic field produced by said smooth muscle electrical activity in said intestine at at least one location external to said abdomen;

determining a measured value of local Basic Electrical Rhythm (BER) frequency from said magnetic field at said at least one location external to said abdomen; and identifying intestinal ischemia at said at least one location when said measured value of said local BER frequency at said at least one location exhibits an interval of arrhythmia.

23. The method of claim 22 wherein said step of identifying intestinal ischemia at said at least one location comprises establishing a nominal value for said local BER frequency at said at least one location and identifying ischemia when said local BER frequency exhibits an interval of arrhythmia in which said BER frequency is at least about twice said nominal value for said local BER frequency.

24. The method of claim 22 wherein said step of identifying intestinal ischemia at said at least one location comprises identifying intestinal ischemia when said measured value of local BER frequency at said one location exhibits an interval of arrhythmia in which said BER frequency is between 24 and 180 cpm.

* * * * *